United States Patent [19]

Ricchio et al.

[11] Patent Number: 5,223,222

[45] Date of Patent: Jun. 29, 1993

[54] AUTOMATIC CHEMISTRY ANALYZER

[75] Inventors: Samuel G. Ricchio, Fullerton; Delbert D. Jackson, Placentia; Stephen F. Barker, La Mirada; Edmund E. Buzza, Fullerton; Frank R. Shu, La Habra Heights; John E. Stone, Riverside, all of Calif.

[73] Assignee: Beckman Instruments, Inc., Fullerton, Calif.

[21] Appl. No.: 811,682

[22] Filed: Jan. 30, 1992

Related U.S. Application Data

[62] Division of Ser. No. 322,807, Mar. 13, 1989, Pat. No. 5,130,095.

[51] Int. Cl.$^5$ .................. G01N 27/403; G01N 35/08
[52] U.S. Cl. ...................... 422/63; 204/409; 204/410; 204/411; 422/81; 422/100; 422/103
[58] Field of Search .................. 422/63, 100, 103, 81; 204/409-411

[56] References Cited

U.S. PATENT DOCUMENTS

| | | |
|---|---|---|
| 3,186,799 | 6/1965 | Hach . |
| 3,327,520 | 6/1967 | Stapp . |
| 3,604,267 | 9/1971 | Johns . |
| 3,719,086 | 3/1974 | Bannister . |
| 3,788,816 | 1/1980 | Rohrbaugh . |
| 3,869,068 | 3/1975 | Chen ...................... 222/148 |
| 3,902,371 | 9/1975 | Hooper . |
| 3,911,749 | 10/1975 | Hendry . |
| 3,964,864 | 6/1976 | Dahms . |
| 3,997,420 | 12/1976 | Buzza . |
| 4,019,861 | 4/1977 | Dahms . |
| 4,036,722 | 7/1977 | Brushwyler et al. . |
| 4,086,061 | 4/1978 | Hoffa . |
| 4,170,523 | 10/1979 | Buzza . |
| 4,199,988 | 4/1980 | Riegger . |
| 4,202,747 | 5/1980 | Buzza . |
| 4,218,197 | 8/1980 | Mayer ...................... 417/422 |
| 4,259,289 | 3/1981 | Curry ...................... 422/64 |
| 4,297,903 | 11/1981 | Buzza ...................... 73/864.22 |
| 4,361,540 | 11/1982 | Weinberg et al. ........... 422/98 X |
| 4,397,725 | 8/1983 | Enzer et al. ............... 422/55 X |
| 4,399,711 | 8/1983 | Klein ...................... 73/864.16 |
| 4,419,903 | 12/1983 | Jackson ...................... 73/864.01 |
| 4,463,615 | 8/1984 | Buzza ...................... 73/863.32 |
| 4,490,234 | 12/1984 | Buzza ...................... 204/409 |
| 4,621,534 | 11/1986 | Munari ...................... 73/864.86 |
| 4,683,212 | 7/1987 | Uffenheimer ............... 422/81 X |
| 4,705,667 | 11/1987 | Marsoner ...................... 422/80 |
| 4,919,887 | 4/1990 | Wakatake ...................... 422/67 |

FOREIGN PATENT DOCUMENTS

| | | |
|---|---|---|
| 0107631 | 5/1984 | European Pat. Off. . |
| 0299659 | 1/1989 | European Pat. Off. . |
| 3502546 | 11/1973 | Fed. Rep. of Germany . |
| 2025900A | 3/1968 | United Kingdom . |

OTHER PUBLICATIONS

System E4A Operating Manual, Beckman Instruments, Inc., Clinical Instruments Division, Brea, California, Section Three, Principles of Operation, pp. 3-1 through 3-8.

IBM Technical Disclosure Bulletin dated Nov., 1983, vol. 26, No. 6.

Primary Examiner—Jill A. Johnston
Attorney, Agent, or Firm—William H. May; Gary T. Hampson; Charles Berman

[57] ABSTRACT

An automatic chemistry analyzer includes a flow cell mounted so that flow through the cell and tubing connected to the cell is visible from the front of the housing. The electrolytes to the cell are removably plugged into the cell from their rear. The probe aspirating sample fluid into an injection cell is simultaneously washed by diluent and the diluent mixes with the fluid sample. Waste fluid from the flow cell is fed to a basin which then feeds under gravity to a waste drain. A ratio pump is formed by selected syringes which are band driven to deliver accurately prerequisite volumes of reagents to the flow cell. The solution ground to the system is on the inlet line for sample adjacent the entrance to the flow cell of fluid thereby minimizing electronic noise. Only two motive means are necessary, one to effect horizontal and rotational movement of the sample tray, and a second to effect vertical motion of a crane mounted probe operative between sample cups and an injection cell.

7 Claims, 7 Drawing Sheets

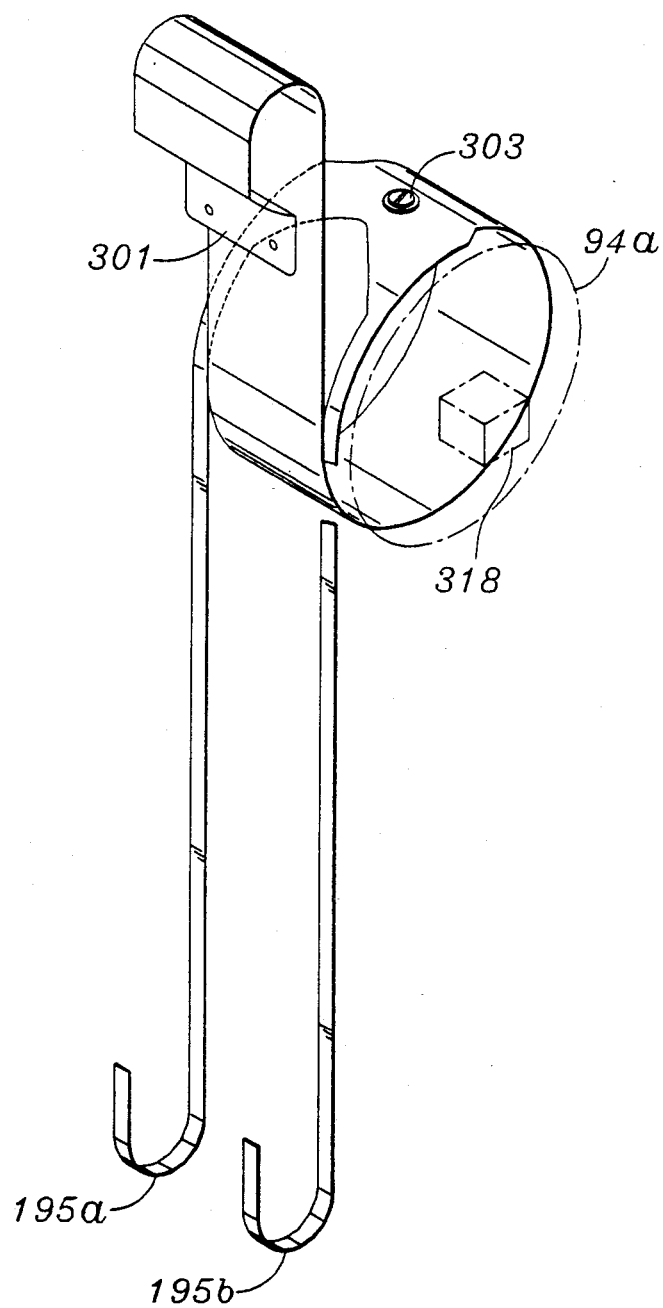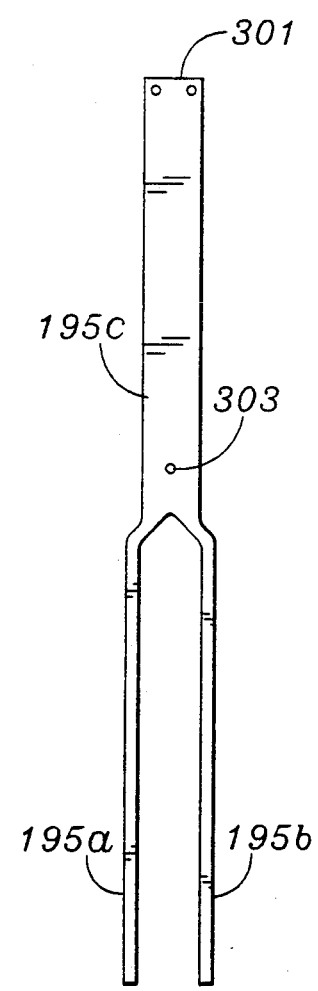
FIG. 12
FIG. 13

AUTOMATIC CHEMISTRY ANALYZER

RELATED APPLICATIONS

This is a divisional of application Ser. No. 07/322,807, filed Mar. 13, 1989, now U.S. Pat. No. 5,130,095.

This invention is related to inventions and disclosures which are the subject of application Ser. Nos. 07/322,814, filed Mar. 13, 1989, now abandoned, 07/322,802, filed Mar. 13, 1989, now U.S. Pat. No. 5,182,083, 07/322,810, filed Mar. 13, 1989, now U.S. Pat. No. 4,915,713, 07/322,811, filed Mar. 13, 1989, now U.S. Pat. No. 5,130,010, 07/322,812, filed Mar. 13, 1989, now abandoned, and 07/322,813, filed Mar. 13, 1989, now U.S. Pat. No. 5,132,233. All these patent applications were filed contemporaneously with application Ser. No. 07/322,807 and the contents of them all are incorporated by reference herein.

BACKGROUND

This invention relates to the field of automatic analytical instruments. More particularly, the invention is concerned with automatic chemistry analyzer instruments for clinical use. In such instruments, there are sample carousels and sample handling systems.

Different clinical analyzers for automatic chemistry analysis are known. One particular kind uses a plurality of individual analysis modules having open reaction cups. An automated sample probe withdraws sample fluid from samples in containers carried on a carousel. Selected volumes of the sample are distributed to analysis module cups in accordance with the tests selected by the instrument operator.

A different kind of analyzer uses a flow cell through which diluent and reagent flows together with samples for determination of electrolytes in the fluid sample. Usually, four electrolytes, namely, sodium, potassium, chloride, and $CO_2$ are measured. In such analyzers, a pick-up probe extends vertically through a shear valve to aspirate the fluid sample from a sample cup aligned with the probe. The probe is withdrawn into the valve and the lower portion of the valve closes. Diluent from a diluent source flows into the valve, is mixed with the sample from the probe and flows to a flow analysis module.

Each of these different kind of analyzers have their unique advantages in analysis of fluid samples. The flow cell analyzer provides simplified fluid handling and minimizing reagent consumption.

The present invention is particularly concerned with flow cell analyzer systems and means for improving the operation, movement, and visibility of the various components and fluids. One of the difficulties in flow cell analyzers is the problem in monitoring the flow stream through the flow cell. Moreover, the flow cell is often located in a manner that is not easily physically accessible or visible which causes difficulty in maintenance and troubleshooting procedures which increases costs of operation. Moreover, another difficulty associated with the flow cell is the difficulty of injecting sample from the sample cup into an injection cell and draining fluid from the flow cell and subsequently from the system. Multiple pumps and wash facilities are often needed to ensure effective injection and drainage. These considerations increase costs and maintenance requirements.

A further problem arises from the arrangement for injecting reagents into the flow cell. Prior art methods include the use of peristaltic/multistage pumps related so as to develop different pumping ratios. It has been relatively difficult to ensure accurate tolerances with the relative ratios of fluids to be pumped in the system.

Other problems which arise are due to electrical noise within the system, and the need to minimize this noise to ensure accurate results. Different techniques have been employed, including a strategic location of the ground for the system.

Many other characteristics exist in the prior art systems which are in need of improvement. These include the sample handling mechanism, means for moving samples from sample reaction cups to an injection cell, means for and the number and nature of the motive means and the electronic operations. All of these characteristics in the prior art have various limitations.

SUMMARY

The present invention solves problems, and improves on the drawbacks posed, in the prior art by providing an automatic chemistry analyzer with substantially enhanced characteristics.

According to one aspect of the invention, the analyzer for measuring electrolytes in a fluid comprises an instrument housing, a flow cell in the housing, the housing having selectively movably panels formed at least in part by the panels. There is means for passing fluid through the flow cell between an injection cell and a drain. The flow cell is mounted in the housing for visibility, so that on opening of, or moving of, the panels from the housing a substantial length of fluid flow through the flow cell is selectively visible from the location from which the panels are opened or moved.

Preferably, the flow cell is formed between a pair of molded clamping plates of at least partly transparent material thereby to permit visibility through the cell. The flow cell includes electrodes removably plugable into the cell from the rear. This is from behind the flow cell relative to the location of the panels in the housing.

According to another aspect of the invention, there is an injection cell for receiving fluid sample. Means for washing the injection cell and means for adding diluent to the cell are provided whereby there is simultaneous dilution of the sample and washing of the probe.

Preferably the injection cell is mounted together with a waste basin, the waste basin and injection cell being part of a unit. The waste basin empties into the drain and the drain is located below the flow cell, the flow from the waste basin to the drain being under gravity.

In yet a further form of the invention, there is provided fluid sources for the flow cell, the fluid sources being selectively reactive or non-reactive with the fluid sample to permit analysis of the sample. A pump is provided for the fluid sources and sample to the flow cell, the pump including discrete syringes between each respective fluid source and the flow cell. The syringes are collectively band driven by motive means, and selectively are of different volume such that different volumes of fluid can be pumped from the syringes to the flow cell. The different volumes of the syringes are relatively predetermined and as such the syringe-band system forms a ratio pump.

In yet a preferred further aspect of the invention, the solution ground for the system is provided on the fluid sample line located close to the measuring electrode. This is preferably at the bottom of the flow cell, namely, at the inlet of the sample/internal reference and diluent into the flow cell.

In a further preferred aspect of the invention, the sole motion for the probe for transferring fluid from the fluid sample to the injection cell is limited to vertical movement, the probe being operable by the crane in response to a band drive.

The invention is further described with reference to the accompanying detailed description and drawings.

DRAWINGS

FIG. 12 is a perspective view of the forked band about the wheel hub of the ratio pump.

FIG. 13 is a plan front view of the forked band.

DESCRIPTION

Figure 1:
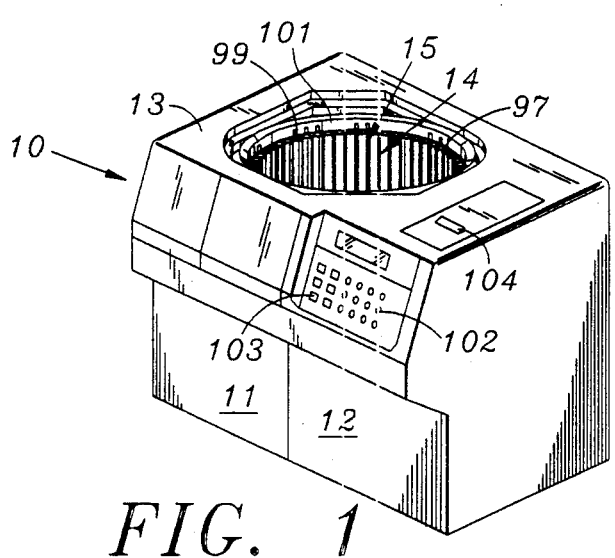
FIG. 1 is a perspective view of an automatic clinical analyzer illustrating a drive wheel and sample wheel mounted in the top of the analyzer.
Figure 3:
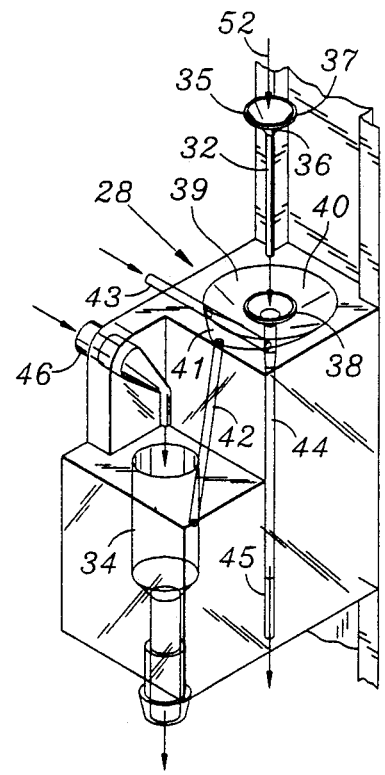
FIG. 3 is a perspective view of an injection cell illustrating a probe in relation to the bore of the cell.

An automatic chemistry analyzer for the measuring of electrolytes in a fluid sample comprises a housing 10 for a flow cell 17. The housing 10 includes two selectively movable panels or doors 11 and 12 mounted on the front side of the housing 10. The doors 11 and 12 form part of the housing 10 and are hinged vertically to open and close and provide access to the interior of the analyzer. In the top face 13 of the housing there is a recessed portion 14 in which a sample wheel 15 is located inside of a drive wheel 16.

Mounted within the housing and facing the front doors 11 and 12 is a flow cell 17. The cell 17 is formed between a pair of molded clamping plates 200 and 201 of at least partly transparent material so as to permit visibility through the flow cell 17. In this manner, the fluid path 18 can be seen from the entry position 19 to the exit position 20 from the flow cell 17.

The flow cell 17 includes an electrode 21 for measuring sodium, an electrode 25 for measuring potassium, an electrode 22 for measuring chloride and an electrode 24 for measuring $CO_2$. An additional spare electrode can be provided for different and other electrolyte measurements, such as lithium. Also, electrode 26 is provided for a reference measurement through a junction 23 to the sample fluid stream. In this manner, the flow cell can selectively have between four to six operative electrodes to measure electrolytes in a fluid sample entering along entrance tube or line 27.

The electrodes 21 through 26 are in the form of spark plug-like elements which adapted to screw fit into the flow cell 17 rearwardly and away from the front doors 11 and 12. In this manner, the electrodes do not impair or hinder the visibility of flow through the flow cell along line 18. The electrodes fit into the rear clamping plate 200. All positions, except $CO_2$, are relative and interchangeable. Output amplifiers plug into the electrodes.

The fluid path 18 is formed only in the rear plate 200. A transparent gasket 202 fits between the plates 200 and 201. Plate 201 is essentially a rec- tangular block of transparent material. Apertures 203 are formed into the plate 200 at right angles relative to the flow path 18. In this manner rear plate 200 can be formed in a simple molding production. Screw formation apertures 204 are cut into the side of the front plate 201 so that the cell 14 can be anchored to a foundation 205 in the structure of the analyzer 10. Pin holes 206 accommodate pins to effect clamping together of the plates 200 and 201.

Fluid for the flow cell 17 is obtained from an injection cell 28. The sample injection cell 28 fits into base plate 29 in the trough of recessed portion 14. In particular, the sample injection cell 28 is located below a target location 30 through which a crane 31 operates. A probe 32 acts to take sample fluid from a sample cup 33A selectively as the cups 33 selectively move into position relative to the crane 31 and the probe 32 mounted on the crane 31. The cups 33 move in cycloidal fashion relative to the top face 13 of the analyzer.

The injection cell 28 is formed as an integral unit together with a waste basin 34. The injection cell 28 is made of substantially transparent material so that the flow through the cell 28 can be visible. The upstream end of the probe 32 includes an seal 35 which includes a truncated section 36. About the seal 35 circumferentially about the truncated section 36 there is a circumferential lip seal 37. The seal 35 mates with a lip 38 about an inlet port 39 to the injection cell 28. The inlet port 39 has a truncated circumferential formation 40 whereby any spillage can drain from the low point of a base 41 about the inlet port 39 through an outlet tube 42 to a waste basin 34.

Diluent fluid enters through tube 43 to be directed into the bore 44 of the injection cell 28. The diluent fluid sweeps down the outside of the probe 32 when the probe is in location in the bore 44. In this manner, the fluid washes the outside of the probe 32 up to the probe tip. Exiting the bore 44 through the tube 45, the diluent and sample are mixed in a predetermined ratio. The mixture passes into tube 27 and through bubble detector 27a, mix chamber 27b, and solenoid operated pinch valve 27c continuing through tube 27 into the bottom of the flow cell 17 through entry port 19.

In some cases, the mix chamber 27b is an integral part of the flow cell 17. Operation of the pinch valve 27c acts to isolate the sample fluid selectively from the fluid sources to the flow cell 17. The solenoid valve 27c is located in the system strategically so as to minimize electronic noise.

The sample and diluent enter through tube 27 at the bottom of the flow cell 15 through entry port 19. The sample fluid, diluent and any other reagents, such as acid and internal reference fluid exit through line 46. These fluids enter through nipple 47, into the waste outlet 48 and then drips into the basin 34. From the basin 34, the outlet 49 is connected with a discharge tube 50 which directs fluids to a low level in housing 10 and subsequently to the drain 51. This waste fluid drains under gravity action. No pumping is necessary of fluid from the basin 34 to the drain 51.

The diluent for mixing with the fluid sample washes the outside of the probe 32 and its tip. This also avoids a further pumping cycle and associated component parts. The diluent flow about the probe 32 is effected by the pumping of the ratio pump.

The flow cell 17 requires various fluid sources to permit measurement of electrolytes. The fluid sources are an acid reagent 53, an internal reference fluid 54, and an electrolyte diluent 55. These are contained in bottles with tubes or pipes 56, 57 and 58 entering the bottles and extending, at least partially towards the bottom of the bottles 59, 60 and 61. An internal reference fluid is the relatively smallest volume of these three fluids. The outlet from each of these bottles 59, 60 and 61 pass respectively along lines 62, 63 and 64 to a ratio pump indicated generally with numeral 65.

Along the tubes 62, 63, and 64 and the ratio pump 65 there are valves 66, 67 and 68 which are respectively connected to the bottles 59, 60 and 61. The valves 66, 67 and 68 are solenoid valve means. They include exit pipes 69, 70 and 71 which are connected respectively to syringes 72, 73 and 74. Exit pipes 75, 76 and 77 are respectively connected in the line between the solenoid valves 66, 67 and 68 and the outlets 78, 79 and 80 from the syringes 72, 73 and 74, respectively.

The syringes include pistons 81, 82 and 83 which are driven by stems 84, 85 and 86, respectively. As the pistons 81, 82 and 83 move upwardly in the respective cylindrical bodies 87, 88 and 89 of the syringes 72, 73 and 74 fluid is pumped out of the exits 78, 79 and 80 of the syringes. The solenoid valves 66, 67 and 68 cooperate with the syringes 78, 79 and 80 such that as the pistons 81, 82 and 83 move respectively upwardly and downwardly, fluid can be pumped into the syringes 72, 73 and 74 or from the syringes 72, 73 and 74. When being pumped from the syringe 72, fluid exits along the fluid outlet tube 90. The fluid exit from the syringe 73 exits through tube 91, and the fluid outlet from syringe exits along the outlet tube 92.

The syringe stems 84, 85 and 86 are driven by a band drive. This band drive is formed by a drive motor 93a which turns a pair of drive hubs 94a and 95a which wrap bands 96a and 97a up and around the peripheral outer circumferences 98a and 99a of the respective drive hubs 94a and 95a. The bands 96a and 97a are forked or split over about half of their length so that there are strip side components 195a and 195b and a central component 195c. The bands 96a and 97a are connected at one free end 301 with a helical springs 302 which counteracts the wrap up force from the drive hubs 94a and 95a. The bands 96a and 97a are anchored at about their central position 303 to the circumferential periphery of the drive hubs 94a and 95a. The opposite ends 304 of the springs 302 are anchored to a bracket 305 in contact with pins 316 attached to carriage 306.

The carriage 306 is a vertical plate 307 which moves upwardly and downwardly in guiderails 308 and 309 on either side of a vertical mounting bracket 310 of the ratio pump 65. The plate 307 has a set of four wheels 311, 312, 313 and 314 located at the corners of the plate 307 for guiding the plate 307 upwardly and downwardly as required under the action of the drive hubs 94a and 95a. The springs 302 remain taut and move upwardly and downwardly with the plate 307. A horizontal slot 325 through the plate 307 permits the bands 96a and 97a to pass from the one side of the plate 307 to the opposite side and then wrap around the top of the plate 307. The bands 96a and 97a in turn pass downwardly under the drive hubs 94a and 95a and then become affixed at anchorages 303. The split portions 195a and 195b, on the one hand, and the central portion 306 effectively wrap around different half portions of the respective hubs 94a and 95a.

The split sections 195a and 195b extend from the respective drive hubs 94a and 95a downwardly and underneath the base 305 of the carriage 306 and are anchored at 320 to the carriage plate 307. The central portion 306 of the bands 96a and 97a extend from the hubs 94a and 95a over the top 322 of the plate 307 and through slot 325.

At the base 305 of the carriage 306 there are horizontal apertures 315 through which pins 316 pass for connection with the free ends 317 of the piston stems 84, 85 and 86, respectively. There are three pins 316 to connect the syringes which are mounted on the side of the vertical mounting bracket 310 opposite to the carriage plate 307.

Figure 7:
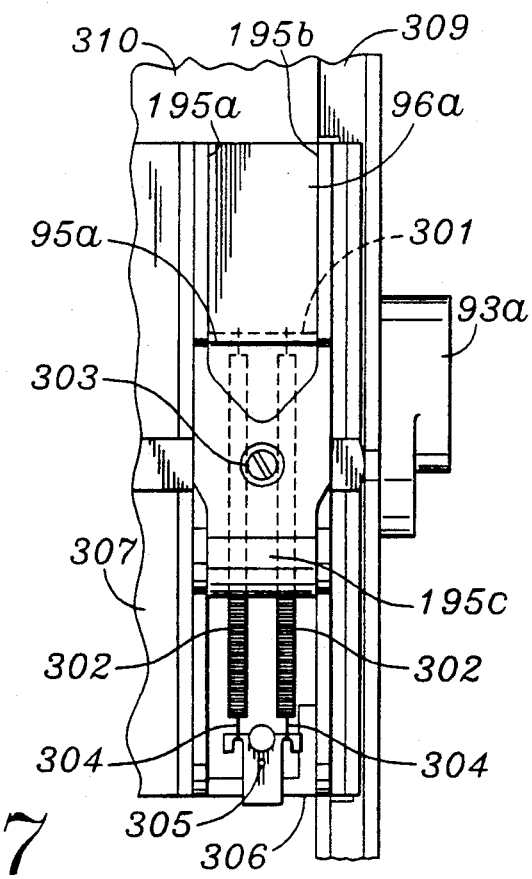
FIG. 7 is a partial elevational view of a band drive for the syringes of the ratio pump.
Figure 8:
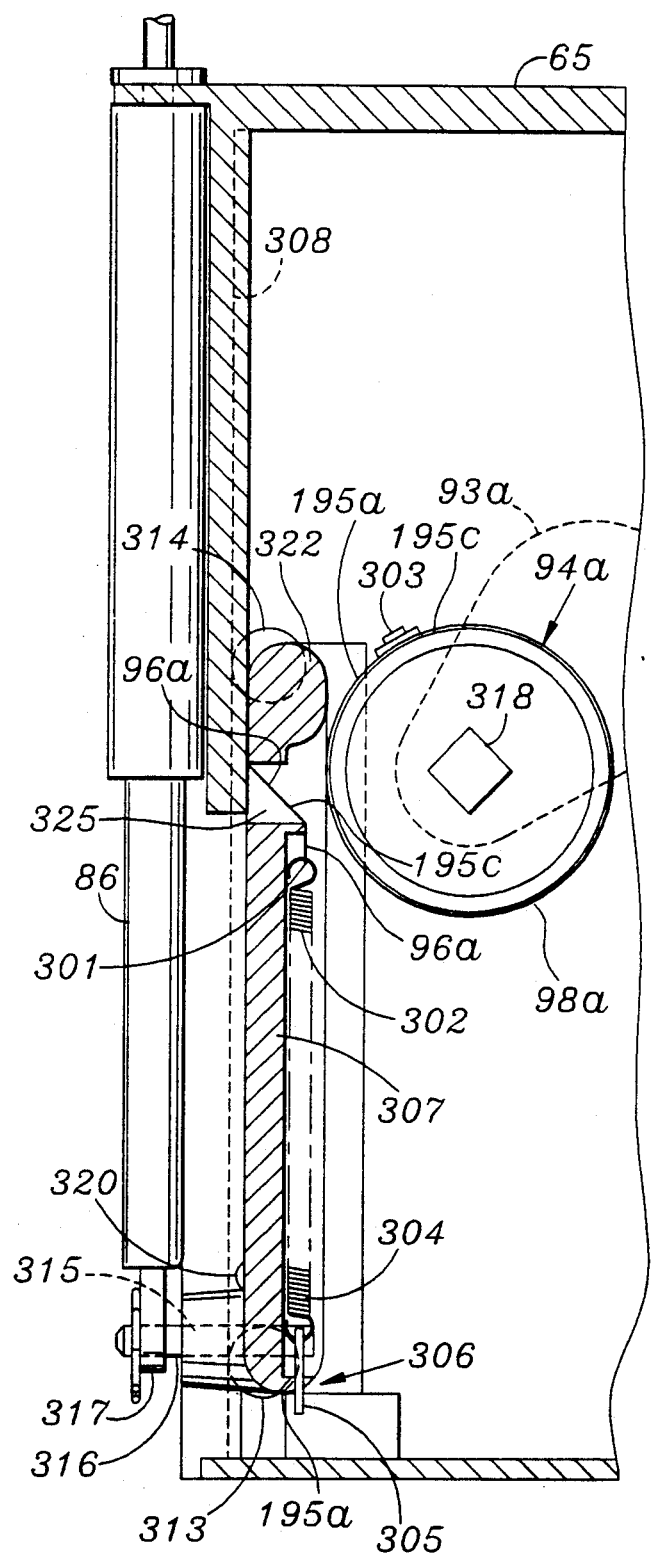
FIG. 8 is a side view partly in section, showing the ratio pump with the band drive system connected with the syringes.
Figure 9:
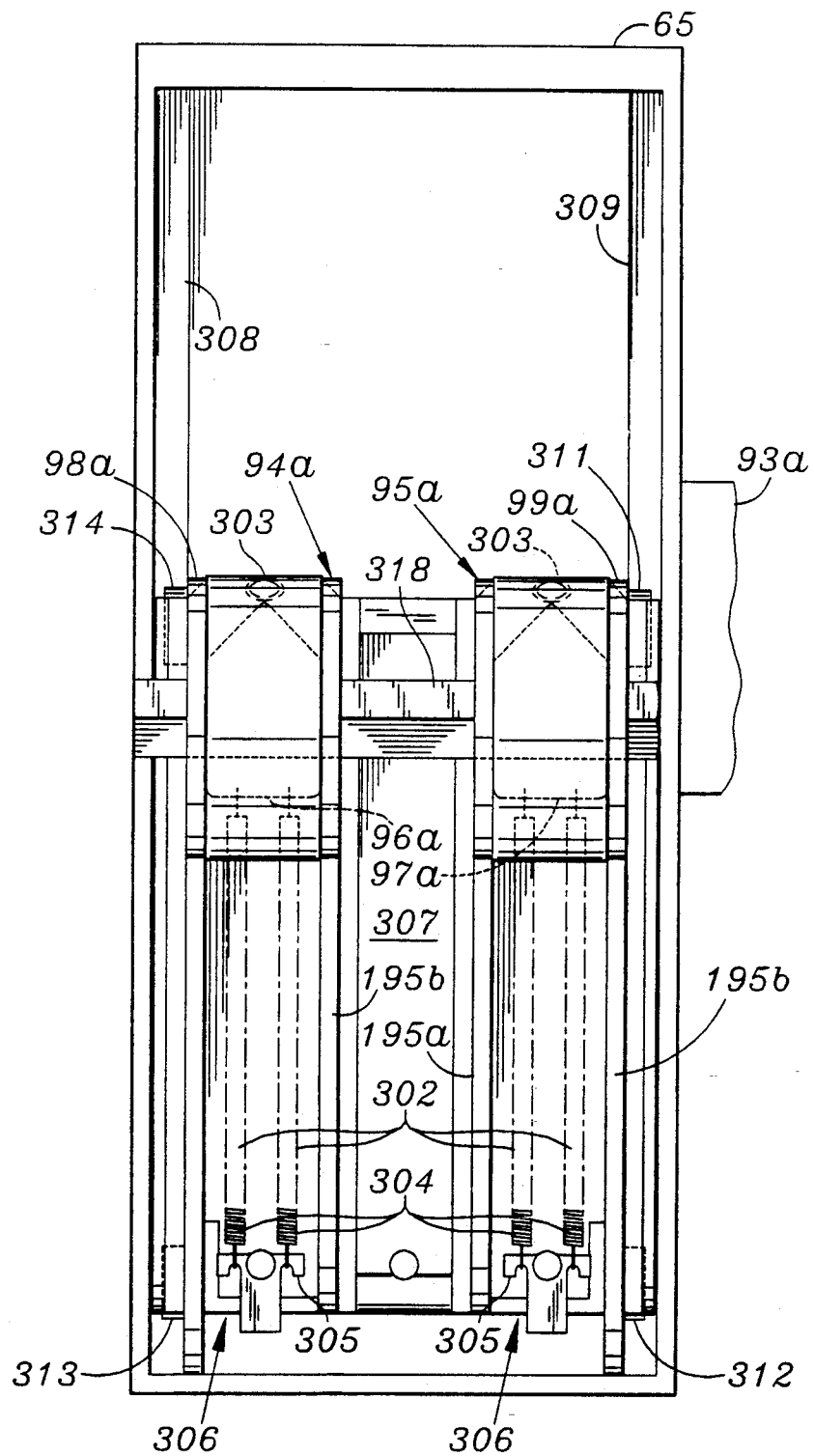
FIG. 9 is a rear elevational view of the ratio pump illustrating the band drive for the syringes in a pump position relatively different to that shown in FIG. 7.
Figure 10:
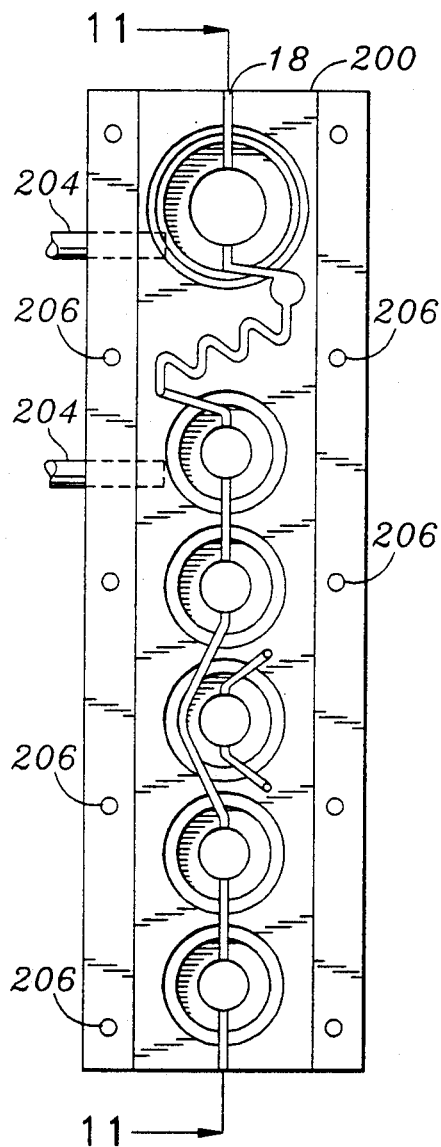
FIG. 10 is a plan front view of the rear plate of the flow cell.
Figure 11:
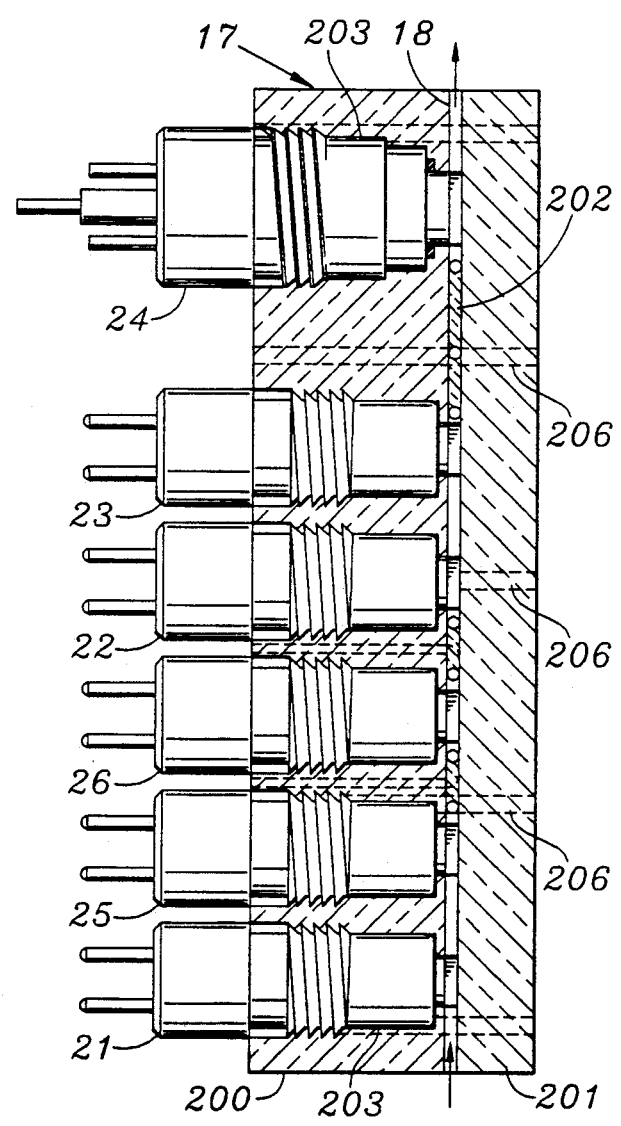
FIG. 11 is a sectional side view of the plates of the flow cell with the electrodes indicated in position in the rear plate of the cell.

In FIG. 7 the carriage 306 with plate 307 is shown in an elevated position, namely in a position where the piston stems 84, 85 and 86 are within the cylinders of the syringes 72, 73 and 74. In this position the drive hubs 94a and 95a have been turned about 270° clockwise relative to the depiction of the position of the hubs 94a and 95a in FIGS. 8 and 9. A square shaft 318 transmits the rotational effect from the drive motor 93a to the drive hubs 94a and 95a.

The band drives for the ratio pump 65 syringes 72, 73 and 74 and for the crane 31 are similar. The drive mechanism including motor and drive hubs for the ratio pump 65 and crane 31 are also similar.

The syringe 73 is relatively smaller in volume than that for syringes 72 and 74. This would correspond to the requisite amounts of reagents necessary for the flow cell 17. Accordingly, the acid reagent and electrolyte diluent are greater than the internal reference fluid. In this manner, the correct proportions of source fluids can be pumped from the ratio pump 65 to the flow cell 17.

The outlet of the acid reagent is directed along tube 90 to a position in line 18 of the flow cell 17 at the start of the mixing serpentine above electrode 23. The internal reference outlet tube 91 is directed to the inlet to probe 32 so that the internal reference can be selectively added to the probe 32 as required. The outlet from the diluent is directed along path 92 to the inlet tube 43 of the injection cell 28 to be mixed with the sample fluid 52 in the bore 44 in addition to washing the outside surface of the probe 32 and its tip. The tube 92 is directed through the reference electrode 26 and the salt bridge 23 en route to the inlet 43 to the injection cell 28.

The internal system reference for the flow cell is a Na or a pH reference. When the internal system reference is Na then utilizing a known concentration of Na is in the diluent fluid.

In order to minimize electronic noise arising from the flow cell 17, a system ground 93 is applied to the flow cell near the inlet end of 19. By having the system ground as close as possible to the measuring electrode, namely, near the bottom of the flow cell 17, the electronic noise and interference is minimized. The system ground 93 is on the inlet line of flow cell 17.

The carbon dioxide electrode 24 requires an alkaline buffer 105 which is fed from container 106 through a debubbler or degassing unit 107 to enter into a tube 108. The liquid or fluid passes from the electrode 24 into an exit tube 109. Tube 109 feeds back to the container 106, the tube 109 entering the container 106 through inlet 110. Gas removed from the liquid through the debubbler 107 is returned at a lower flow rate to the container 106 through pipe 108 in the form of gas or air entrained liquid. This is constituted as the bubbles 111 entering through the port 112. Peristaltic pumps 114 effects movement of the fluid in the degassing system.

Figure 5:
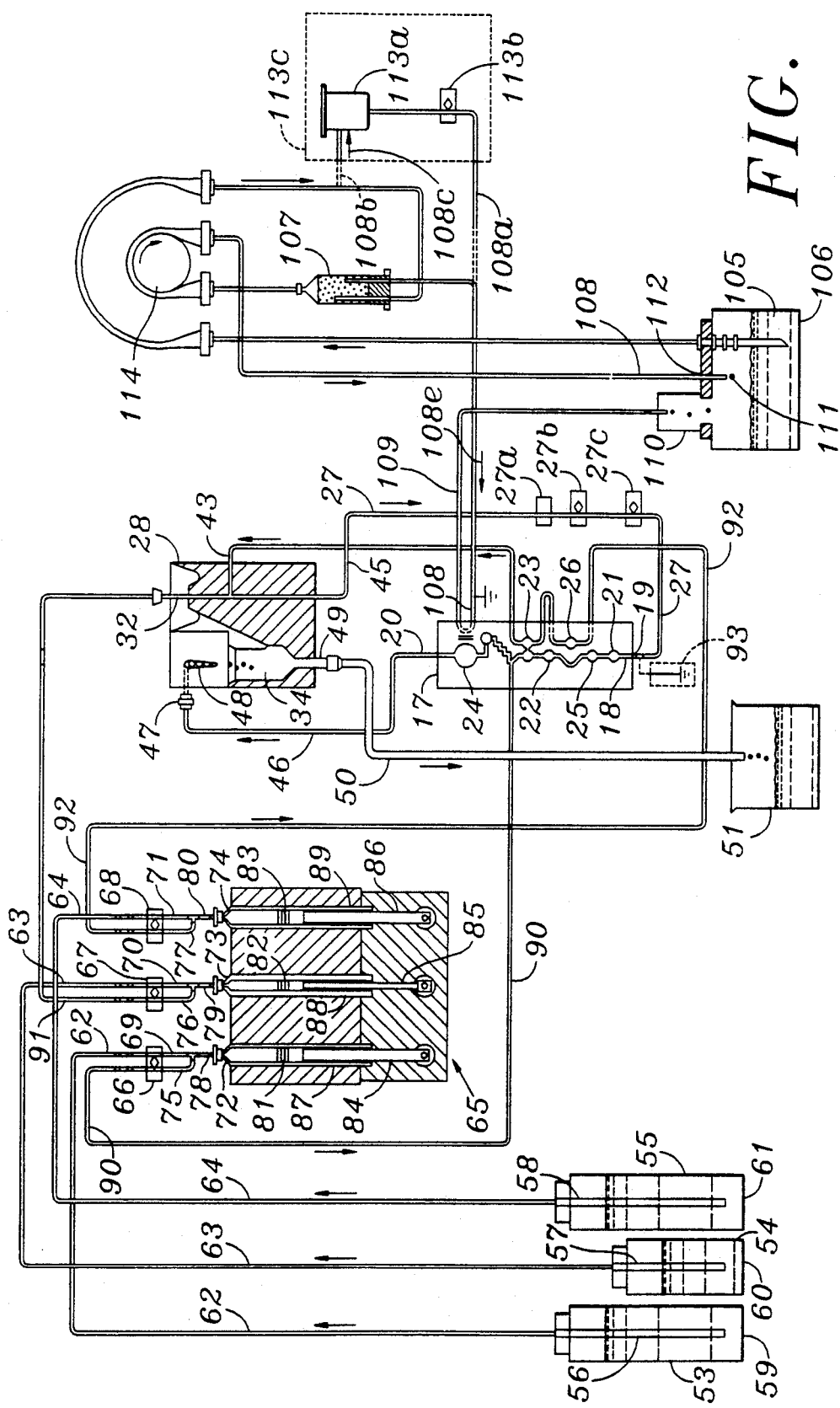
FIG. 5 is a flow diagram of a chemistry analyzer showing the fluid path relationship to various physical components of the system.
Figure 6:
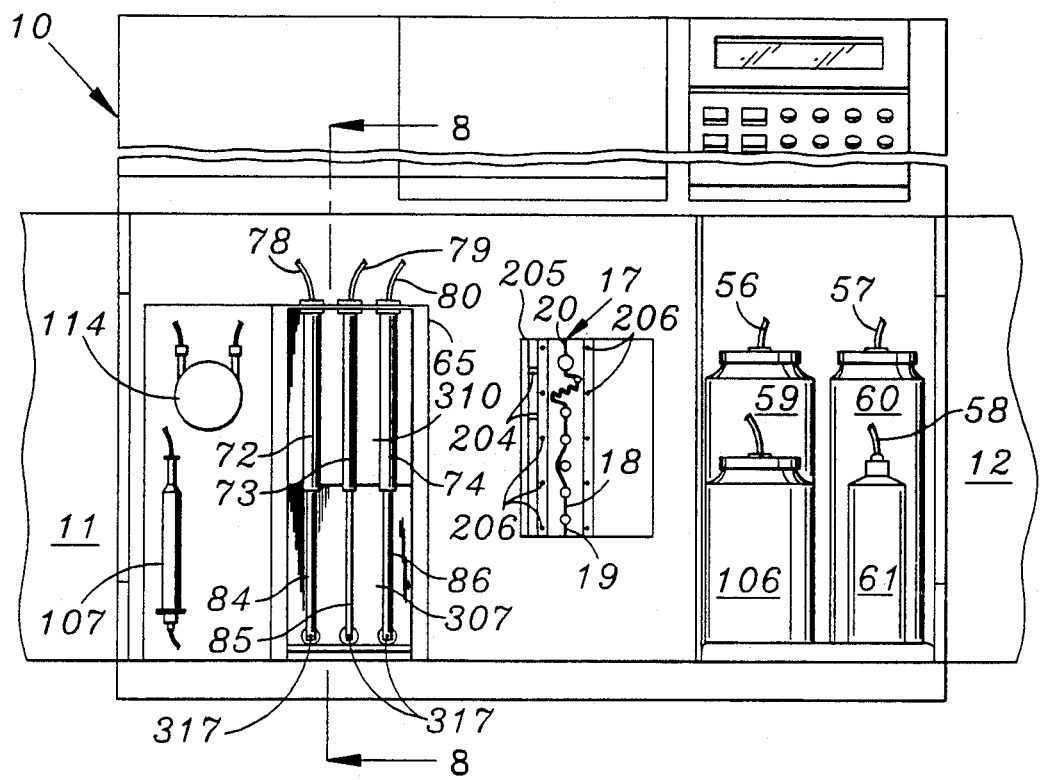
FIG. 6 is a front elevational view of the analyzer with the front doors open and showing the relative layout of some components.

An alternate system for the $CO_2$ alkaline buffer fluid 105 is also shown in FIG. 5 adjacent to the above described debubbler system, the system being in the dashed box 113c.

This alternate system replaces debubbler 107, and its associate parts 111 and 112, including the smaller peristaltic pump tube 108. In its place, a damper chamber 113a and pinch valve 113b are installed as shown. Line 108 is re-routed in and out of the damper 113a, through pinch valve 113b and into the $CO_2$ electrode as shown. Line 108b will direct fluid into the chamber 113a, and line 108a will redirect fluid to the $CO_2$ electrode. The flow line will follow arrows 108c and 108d.

A removable, self-aligning salt bridge 23 is provided in the flow cell 17 between the location for the electrode 22 and the $CO_2$ electrode 24. Diluent solution is pumped by the ratio pump along tube 92 to the reference electrode 26 then to the reference side of the salt bridge 23. This provides both for an appropriate solution for the reference electrode and electrical connection to the sample flow path.

Figure 2:
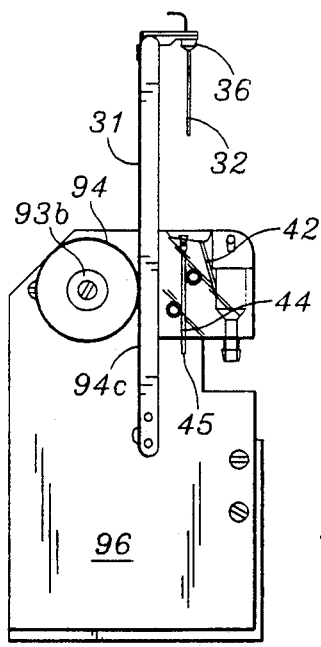
FIG. 2 is a side view of a crane mounting with a probe, the probe being operative between sample cups or tubes in the sample wheel and an injection cell in the analyzer.
Figure 4:
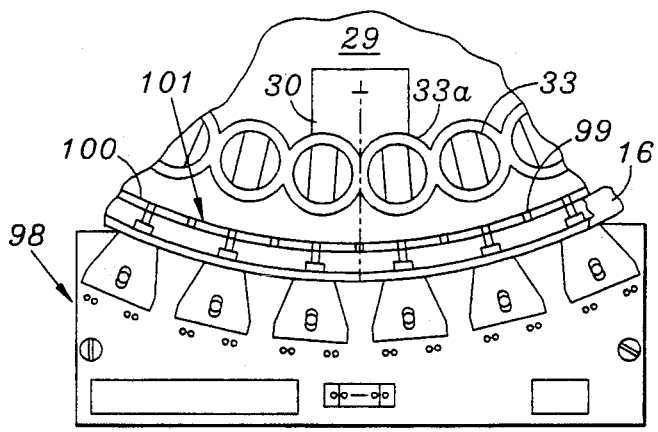
FIG. 4 is a partial plan view of the analyzer illustrating a part of the sample wheel, drive wheel, and sensors for coding the sample wheel located adjacent to the sample wheel and drive wheel.

The crane 31 illustrated in FIG. 2, moves only in a vertical direction as driven by the band 94c which wraps around the circumference of the driv wheel 94 driven by the motor 93b. The motor 93b and drive wheel 94c are mounted on a bracket 96 which is located operatively relative to the target zone 30. In this manner, the crane 31 can move vertically upwardly and downwardly and selectively inject the probe 32 into the bore 44 of the injection cell. Selectively, when the sample cups or tubes 33 are located over the target location 30, the probe 32 enters a sample cup. When the sample cup 33A is removed, the probe 32 can enter the bore 44 of the injection cell 28. The seal 35 and lip 37 about the probe 32 and mates with the lip 38 at the inlet port 39 to the bore 44.

The sample tray 15 moves horizontally under cycloidal action into and away from the target location 30 while the probe 32 moves vertically under the action of the band 94c and its drive.

The operational sequence includes crane means 31 for raising the probe 32 above the sample tray level 97. A motor system operating a drive wheel 16 moves the sample tray 15 into a position below the probe 32. The crane 31 then lowers the probe 32 into a sample element 33 in the sample tray 15, where a sample is drawn into the probe 32. The crane means 31 then raises the probe 32 above the sample tray 15 and the sample tray 15 is moved laterally and transversely away from being underneath the probe 32. The crane means 31 then lowers the probe 32 downwardly to the injection cell 28 where there are means for ejecting or dispensing the sample fluid from the probe 32 into the bore 44 of the injection cell 28. The crane 31 moves the probe 32 upwardly and the cycle is repeated with different sample cups 33 moved into and from the target location 30.

Adjacent to the outside of the periphery of the sample tray 15 is a sensor unit 98 which operates optically to sense the location of the sample wheel tray 15 in different positions relative to the target location 30. Apertures 99 and reflective protrusions or flags 100 in the wall 101 of the sample wheel 15 provide for reflectance and non-reflectance of an optical signal from the sensor unit 98. The apertures 99 and reflective protrusions or flags 100 are related in predetermined coding fashion to particular cells 33. This provides for indexing and identification of various cells or cups 33, about the sample wheel tray 15.

The timing of the sequences, which also includes the motion of the mechanical parts is under microprocessor control. This control can be regulated by keyboard input 102 and the display 103 which indicates the sequence and the status of the instrument 10. Outputted hard copy of analytical results can be obtained from printer exit slot 104. This gives a reading of analytical data about the system or samples as required.

Many other forms of the invention exist, each differing from the others in matters of detail only. The scope of the invention is to be determined solely by the appended claims.

We claim:

1. A clinical analyzer for measurement of electrolytes in a flow cell comprising different means for providing a sample to a flow cell, different discrete fluid sources for the flow cell, the discrete fluid sources being selectively reactive with the fluid sample passing through the flow cell thereby to permit sample analysis, a pump between the fluid sources and the flow cell for selectively pumping fluid into the flow cell, the pump including discrete syringes connected between the discrete fluid sources and the flow cell, the syringes including stems, a band drive for operating a string of respective syringes, and means for measuring reaction of the sample and the fluid sources thereby to obtain an analysis of the sample.

2. An analyzer as claimed in claim 1 including valve means connecting each of said discrete syringes between a respective fluid source and between each syringe and the flow cell.

3. An analyzer as claimed in claim 2 wherein the valve means includes a plurality of solenoid valves each of said solenoid valves connected with a respective syringe, a direct or indirect feed line from a respective fluid source and a feed line to the flow cell.

4. An analyzer as claimed in claim 1 wherein the band drive includes a band wrapped about a drive hub, the drive hub being operated by a motor, a free end of the band activating the stems of respective syringes to operate the syringes as the motor moves the band relative to the drive hub.

5. An analyzer as claimed in claim 4 wherein the band drive is common for all syringes and wherein the common band drive simultaneously operates the steering of respective syringes, and wherein the syringes are selectively of different volume such that operation of the band drive causes the syringes to pass different volumes of fluid between the respective fluid source and the flow cell.

6. An analyzer as claimed in claim 1 wherein the fluid sources are diluent, acid and internal reference fluids.

7. An analyzer as claimed in claim 4 wherein the band is split longitudinally and the band drives a common plate relatively vertically, the plating connected to the stems of respective syringes through pin means.

* * * * *